United States Patent [19]

Hesse

[11] Patent Number: Plant 6,204

[45] Date of Patent: Jun. 14, 1988

[54] CHRYSANTHEMUM PLANT NAMED DARK PARASOL

[75] Inventor: Peter S. Hesse, Brandenton, Fla.

[73] Assignee: Ball PanAm Plant Company, Parrish, Fla.

[21] Appl. No.: 873,792

[22] Filed: Jun. 12, 1986

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Dark Parasol characterized by its large dark purple ray florets which vary in shape from completely flat to spoon to completely quilled, white quills near disc florets, resistance to fading at high temperatures, compact habit and even flowering, superior breaking, yellow-green to yellow disc florets, and its generally eight week flowering response.

1 Drawing Sheet

The present invention comprises a new and distinct cultivar of *Chrysanthemum morifolium*, Ramat., hereinafter referred to by the cultivar name Dark Parasol.

Dark Parasol was originated from a mutation resulting from a controlled radiation program in Parrish, Fla. in 1983, with the purpose of the radiation program being to expand the color range of the parent cultivar Parasol, disclosed in a pending application of applicant and Leonard H. Shoesmith. Tissue cultured plants of Parasol were given 900 rads of X-ray energy in the radiation program.

Dark Parasol was discovered and selected as one flowering plant within the population of the irradiated plants of the parent cultivar Parasol by Peter S. Hesse in March of 1983 in a controlled environment in Parrish, Fla.

The first act of asexual reproduction of Dark Parasol was accomplished when vegetative cuttings were taken from the initial selection in August of 1983 in a controlled environment in Parrish, Fla. by a technician working under formulations established and supervised by Peter S. Hesse. Horticultural examination of selected units initiated in October of 1983 has demonstrated that the combination of characteristics as herein disclosed for Dark Parasol are firmly fixed and are retained through successive generations of asexual reproduction.

Dark Parasol has not been observed under all possible environmental conditions. The phenotype may vary significantly with variations in environment such as temperature, light intensity and day length. The following observations, measurements and comparisons describe plants grown in Parrish, Fla. and West Chicago, Ill. under greenhouse conditions which approximate those generally used in commercial practice.

The following traits have been repeatedly observed and are determined to be basic characteristics of Dark Parasol, which in combination distinguish this Chrysanthemum as a new and distinct cultivar:

1. Eight week flowering response, 2–3 days later than Parasol.
2. More compact and even flowering than Parasol.
3. 3–4 breaks per pinch, producing a full plant.
4. Flat capitulum, 80–120 mm in diameter with about 33 ray florets per flower.
5. Ray florets are large, up to 60 mm long and 12 mm wide.

6. Ray florets are purple in color and range in shape from completely flat to spoon to completely quilled.
7. Dark purple flowers are more resistant than the flowers of Parasol to fading at high temperatures.
8. Leaves are large (up to 130 mm long and 100 mm wide) and generally ellipical, with deeply lobed and slightly serrated margins.
9. Yellow green (immature) to yellow (mature) disc floret color.
10. Plants finish about 30 cm above the edge of the pot.

Of the many commercial cultivars known to the present inventor, the most similar in comparison to Dark Parasol is Parasol. In comparison to Parasol, Dark Parasol has a more compact habit, is more even flowering, and has a more uniform purple color intermediate the relatively darker and lighter shades of Parasol produced under low (58°–75° F.) and high (75°–85° F.) night temperatures, respectively. Dark Parasol also retains its color better than Parasol at high temperatures. Other characteristics of Dark Parasol are generally similar to those same characteristics of Parasol.

The accompanying photographic drawing shows typical inflorescence and foliage characteristics of Dark Parasol. The drawing comprises a black and white photograph with one flower being colored to depict tube and ray floret color.

In the following description, color references are made to The Royal Horticultural Society Colour Chart. The color values were determined between Noon and 1 p.m. on May 21, 1986 under fluorescent light at Bradenton, Fla.

Classification:

*Botanical.*—*Chrysanthemum morifolium*, Ramat., cv Dark Parasol.

*Commercial.*—Pot mum.

INFLORESCENCE

A. Capitulum:

*Form.*—Flat.

*Type.*—Novelty daisy or single.

*Diameter Across Face.*—80–120 mm.

B. Corolla of ray florets:

*Color (general tonality from a distance of three meters).*—Dark Purple.

*Color.*—Tubes are white, 155D; upper surface of ray florets 78A-B, under surface of ray florets varying from 75A to 75D.

C. Corolla of disc florets:

*Color (mature).*—Yellow.

*Color (immature).*—Yellow-green.

D. Reproductive organs:

*Androecium.*—Present in all disc florets; many.

*Gynoecium.*—Present in all ray florets; many.

PLANT

A. General appearance:

*Height.*—Plants finish about 30 cm above the edge of the pot.

B. Foliage:

*Color (upper surface).*—147A.

*Color (under surface).*—147B.

*Shape.*—Generally elliptical; with deeply lobed and serrated margins.

I claim:

1. A new and distinct cultivar of Chrysanthemum plant named Dark Parasol, as described and illustrated, and characterized by its large dark purple ray florets which vary in shape from completely flat to spoon to completely quilled, white quills near disc florets, resistance to fading at high temperatures, compact habit and even flowering, superior breaking, yellow-green to yellow disc florets, and its generally eight week flowering response.

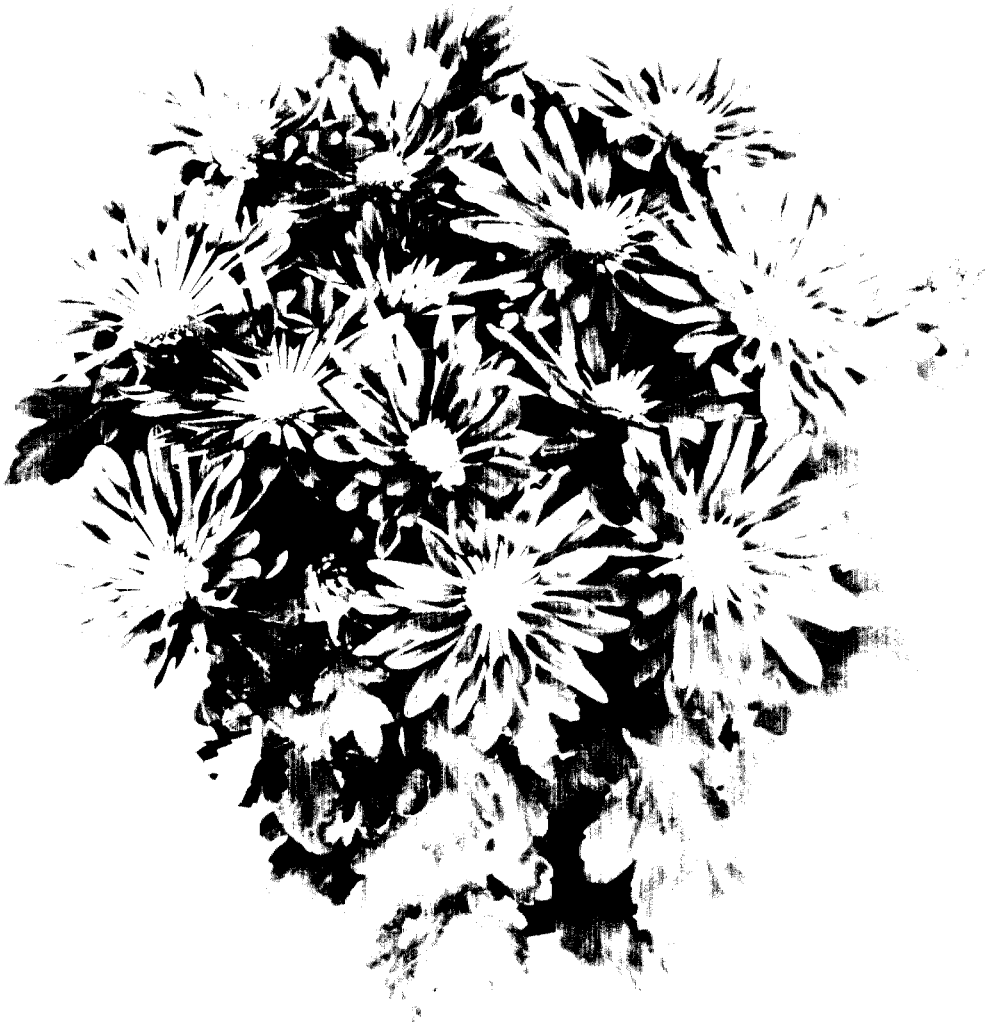

* * * * *